(12) United States Patent
Palmer et al.

(10) Patent No.: US 6,280,185 B1
(45) Date of Patent: Aug. 28, 2001

(54) ORTHODONTIC APPLIANCE WITH IMPROVED PRECIPITATION HARDENING MARTENSITIC ALLOY

(75) Inventors: John J. Palmer, Monrovia; John S. Kelly, Arcadia; James D. Hansen, Pasadena, all of CA (US)

(73) Assignee: 3M Innovative Properties Company, St. Paul, MI (US)

( * ) Notice: Subject to any disclaimer, the term of this patent is extended or adjusted under 35 U.S.C. 154(b) by 0 days.

(21) Appl. No.: 09/595,664

(22) Filed: Jun. 16, 2000

(51) Int. Cl.$^7$ ........................................... A61C 3/00
(52) U.S. Cl. ................... 433/8; 433/6; 433/17; 433/18; 433/20
(58) Field of Search ............... 433/8, 9, 20, 17, 433/5, 6, 7, 18

(56) References Cited

U.S. PATENT DOCUMENTS

| | | |
|---|---|---|
| Re. 35,863 | 7/1998 | Sachdeva et al. . |
| 4,197,643 | 4/1980 | Burstone et al. . |
| 4,588,380 | 5/1986 | Toll . |
| 4,783,216 | 11/1988 | Kemp, Jr. et al. . |
| 4,943,322 | 7/1990 | Kemp, Jr. et al. . |
| 5,232,361 | 8/1993 | Sachdeva et al. . |
| 5,288,230 | 2/1994 | Nikutowski et al. . |
| 5,334,015 | 8/1994 | Blechman . |
| 5,411,613 * | 5/1995 | Rizk et al. ........................ 148/606 |
| 5,456,599 | 10/1995 | Hanson . |
| 5,474,447 | 12/1995 | Chikami et al. . |
| 5,512,237 | 4/1996 | Stigenberg . |
| 5,573,401 | 11/1996 | Davidson et al. . |
| 5,681,528 * | 10/1997 | Martin et al. ........................ 420/53 |
| 5,714,115 | 2/1998 | Speidel et al. . |
| 5,727,941 | 3/1998 | Kesling . |
| 5,803,728 | 9/1998 | Orikasa et al. . |
| 5,816,801 | 10/1998 | Farzin-Nia et al. . |
| 5,904,480 | 5/1999 | Farzin-Nia et al. . |
| 5,919,041 | 7/1999 | Masumoto et al. . |
| 5,944,517 | 8/1999 | Binder . |
| 5,947,723 | 9/1999 | Mottate et al. . |
| 5,954,501 | 9/1999 | Masumoto et al. . |
| 5,954,724 | 9/1999 | Davidson . |

FOREIGN PATENT DOCUMENTS

| | | |
|---|---|---|
| 0679381 A1 | 11/1995 | (EP) . |
| WO 99/45161 | 9/1999 | (WO) . |
| WO 99/58078 | 11/1999 | (WO) . |

OTHER PUBLICATIONS

"Alloy Data, Custom 455 Stainless", *Carpenter Technology Corporation, Carpenter Steel Division,* (*CarTech*), 10 pages.

Kattus, J.R., "Ferrous Alloys", *Aerospace Structural Metals Handbook*, Mar. 1978.

* cited by examiner

Primary Examiner—Nicholas D. Lucchesi
(74) Attorney, Agent, or Firm—James D. Christoff

(57) ABSTRACT

An orthodontic appliance such as a bracket or buccal tube is made of a stainless steel alloy that includes chromium, nickel and precipitates of titanium. The alloy imparts a relatively high strength to the appliance and is resistant to corrosion. Optionally, the appliance has structural sections that are smaller than corresponding sections of comparable appliances when made of conventional stainless steel alloys used in orthodontic appliances. As a consequence, the appliance is more aesthetic when mounted on a tooth of a patient undergoing treatment.

9 Claims, 4 Drawing Sheets

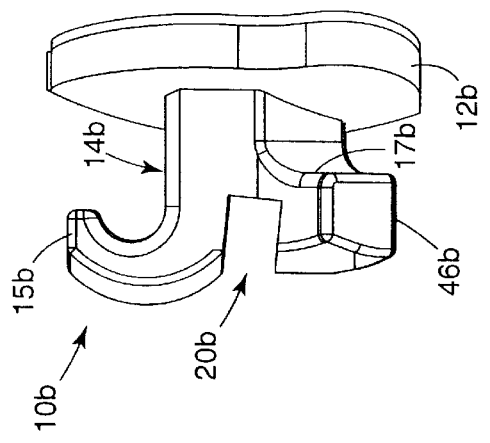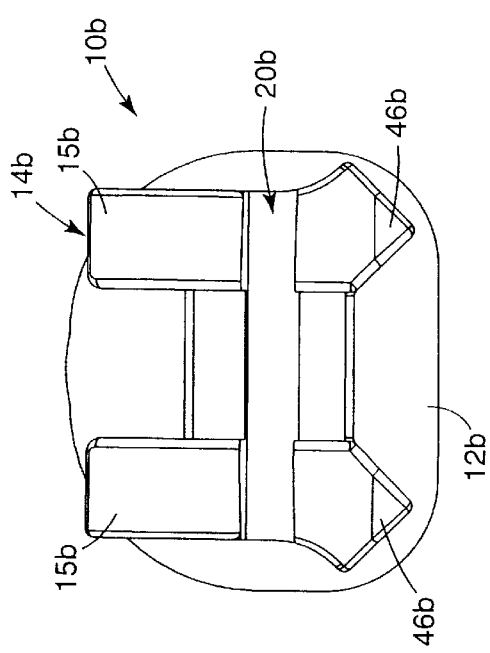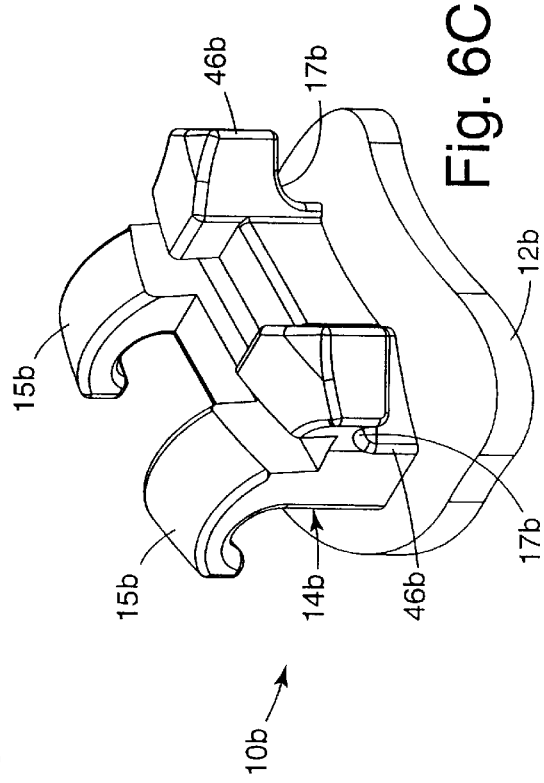

ORTHODONTIC APPLIANCE WITH IMPROVED PRECIPITATION HARDENING MARTENSITIC ALLOY

BACKGROUND OF THE INVENTION

1. Field of the Invention

This invention broadly relates to an appliance that is used in the oral cavity during the course of orthodontic treatment. More particularly, the present invention is directed to an orthodontic appliance that is made at least in part from a precipitation hardening martensitic stainless steel alloy.

2. Description of the Related Art

Orthodontic treatment involves movement of malpositioned teeth to orthodontically correct locations for improved occlusion and an improved aesthetic appearance. In certain types of orthodontic treatment programs, a system of appliances commonly known as "braces" is utilized by the orthodontist to effect movement of the teeth. Typically, braces include a set of tiny appliances known as brackets as well as archwires that are adapted to fit into slots of the brackets.

In many orthodontic treatment programs, a bracket is affixed directly to each of the patient's anterior, cuspid and bicuspid teeth, and buccal tubes are mounted on the patient's molar teeth. An archwire is then ligated into the slot of each bracket using short wire ties or ring-shaped elastomeric ligatures. Ends of the archwire are inserted into passages of the buccal tubes. The archwire forms a track to guide movement of the brackets and hence movement of the associated teeth to desired positions.

Orthodontic brackets are commonly made of metal, plastic or ceramic. Plastic and ceramic brackets that are made of transparent or translucent material are preferred by some patients and practitioners, because the color of the tooth may be visible through the bracket. As a result, such brackets are less noticeable in ordinary view.

However, plastic brackets are often considered unsatisfactory for one reason or another. Plastic material tends to creep and deform over a period of time when subjected to stress. As a consequence, the archwire slot of plastic brackets may widen during use to such an extent that precise control over movement of the teeth is lost. Additionally, some plastic materials tend to stain and discolor when exposed to certain foods and beverages such as mustard, spaghetti sauce, blueberries, coffee, tea and the like.

Orthodontic brackets that are made of ceramic materials are also deemed unsatisfactory by some practitioners and patients. Ceramic materials are generally considered very hard and brittle, and may wear away the enamel of opposing teeth if the brackets contact the enamel as the patient's jaws are closed. Additionally, the ceramic material may tend to fracture if the bracket is subjected to relatively large force, such as when the patient bites into a hard food object such as a peach pit. Certain ceramic brackets are well-constructed and overcome these difficulties, but are somewhat more expensive than brackets made of metallic materials.

As a result, metal brackets remain the appliances of choice for many orthodontists. Metal brackets are relatively low in cost, and yet have sufficient strength to withstand the forces typically encountered during treatment without breakage. Additionally, many practitioners have developed certain treatment techniques after many years of practice, and prefer to keep using metal brackets in their practice so that they can be assured that the teeth will move efficiently to their intended positions and the expected outcome of treatment can be reliably achieved without undue delay.

Over the years, many orthodontic appliances including brackets, buccal tubes and archwires have been made of stainless steel alloys. Examples of such stainless steel alloys include Series 300, Series 400 and 17-4 PH. Such alloys are relatively inexpensive, corrosion resistant and machinable with conventional apparatus.

Other metal alloys have also been suggested for use in orthodontic appliances. For example, U.S. Pat. Nos. 5,947,723 and 5,232,361 describe appliances made of titanium alloys. Orthodontic appliances made of beta-titanium alloys are described in U.S. Pat. No. 4,197,643 and PCT Published Application No. WO 99/45161.

Unfortunately, conventional metal brackets are not considered in general as aesthetic as plastic or ceramic brackets. Many metal brackets are easily visible in use, causing a condition known as a "tin grin" or "metal mouth" that can be a source of embarrassment to the patient. Attempts have been made in the past to make metal brackets less noticeable by reducing the overall size of the brackets, but any significant reduction in size is limited by the strength of the material.

While good results have been obtained in orthodontic treatment programs utilizing appliances made of some of the alloys mentioned above, there is a continuing need in the art for an orthodontic appliance that is made of a metallic alloy and yet is more aesthetic than existing appliances. Furthermore, there is a need in the art to improve existing orthodontic appliances in order to facilitate treatment and reduce the time that would otherwise be needed to achieve the desired results.

SUMMARY OF THE INVENTION

The present invention is directed toward an orthodontic appliance that is made of a precipitation hardening martensitic alloy. The appliance of the invention provides superior results in terms of strength, function and aesthetics in comparison to known appliances made of other alloys. The orthodontic appliance of the present invention is made of a stainless steel alloy that includes precipitates of titanium along with other elements in controlled amounts.

The precipitates of titanium in the appliance impart a significant improvement in strength and resistance to corrosion in the oral environment in comparison to the strength and corrosion resistance of conventional appliances. As an example, conventional appliances made of 17-4 PH stainless steel include precipitates containing aluminum, copper, nickel and/or iron. It has been found that iron-based alloys with precipitates of titanium provide superior resistance to corrosion in the oral environment where saliva and other fluids are present.

In one aspect, the present invention is directed toward an orthodontic appliance that is made of an iron-based alloy that includes precipitates of titanium in an amount effective to strengthen the alloy. In another aspect, the present invention is directed toward an orthodontic bracket that comprises a base, a body extending from the base and an archwire slot extending across the body. The body is made of an iron-based alloy that includes precipitates of titanium in an amount effective to strengthen the alloy.

In another aspect, the present invention is directed toward an orthodontic appliance having a body that is made of a martensitic precipitation hardening stainless steel alloy consisting essentially of, in weight percent, about 10–13% chromium, 9–12% nickel, 1–4% titanium, 0.5–2% molybdnum, 0.001–0.01% boron, and not more than about 1% manganese, not more than 1% silicon, not more than 0.04% carbon, nitrogen or phosphorous, and not more than 0.02% sulfur, with the balance being iron.

Advantageously, the orthodontic appliances of the invention can be constructed of a size significantly smaller than the size of similar appliances made of conventional orthodontic alloys. This reduced size makes the appliances more difficult to see when worn by a patient during the course of treatment, and consequently enhances the aesthetic characteristics of the appliance to a significant extent.

Additionally, the reduced size of the appliances provides many mechanical and functional advantages during the course of treatment. For example, and as explained in more detail below, the reduction in size enables the appliances to have configurations not previously possible to any practical extent. This reduction in size also allows the use of other orthodontic components that are different and/or used differently than previously known. Moreover, the smaller size of the appliance reduces the likelihood of irritation to the patient's oral tissues and unintentional contact with opposing dentition.

Optionally, the orthodontic appliances of the present invention exhibit a color that is different and considered more aesthetic than conventional metallic orthodontic appliances. It has been found that the titanium in the alloy of the present invention can form nitrides under certain conditions during heat treatment in such a manner that a surface layer having a color resembling straw or light gold is produced. The presence of this aesthetic color can be controlled by introducing nitrogen gas into the atmosphere surrounding the appliances during heat treatment so that a significant titanium nitride layer is formed.

These and other aspects of the invention are described in the paragraphs that follow, and examples of the invention are set out in the accompanying drawings.

BRIEF DESCRIPTION OF THE DRAWINGS

FIGS. 6A, 6B and 6C are enlarged front, end and perspective views respectively showing another orthodontic appliance that is constructed in accordance with the present invention.

DETAILED DESCRIPTION OF THE PREFERRED EMBODIMENTS

Figure 1A:
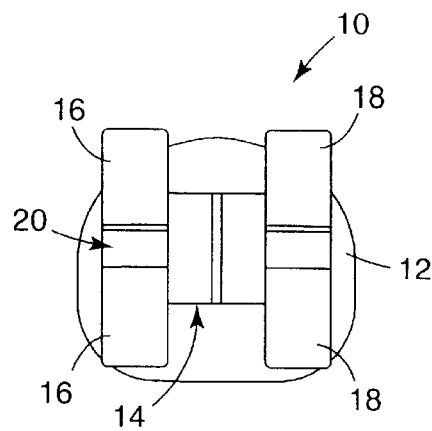
FIGS. 1A, 1B and 1C are front, end and side views respectively of an exemplary prior art orthodontic appliance.

Orthodontic appliances constructed in accordance with the present invention are made at least in part of an iron-based alloy, and preferably a stainless steel alloy, that includes precipitates of titanium in an amount effective to strengthen the alloy. The alloy includes iron as the principal metal along with alloying elements of chromium and nickel. In this application, unless otherwise indicated, "percent" (%) means percent by weight.

The alloy of the orthodontic appliance according to the present invention has a nickel content in the range of about 9% to about 12%, and preferably from about 10.5% to about 11.5%. Chromium is present in the range of about 10% to about 13%, and preferably in the range of about 11% to about 12%. An example of a suitable nickel/chromium combination is 11% nickel and 12% chromium.

The preferred alloy used in the present invention utilizes titanium and nickel in the form of $Ni_3Ti$ intermetallic precipitates to accomplish the majority of the precipitation strengthening. Preferably, the alloy includes titanium in the range of about 1% to about 4%, and more preferably in the range of about 1% to about 2%. The titanium precipitates significantly improve the strength of the alloy and the resulting appliances.

Preferably, a small amount of molybdenum is added to improve the formation of martensite on cooling. The molybdenum also improves the corrosion resistance of the resultant appliance. Preferably, the molybdenum is present in an amount less than about 2%, and more preferably is present in an amount ranging from about 0.5% to about 1.5%.

In addition, a small amount of boron is added to the alloy to act as a grain refiner. The boron also improves the stress corrosion resistance and toughness of the alloy. Boron also improves the hot workability of the alloy. Preferably, the amount of boron is less than about 0.1%, and more preferably is in the range of about 0.001% to about 0.01%.

Additionally, the alloy of the orthodontic appliances of the present invention may optionally contain copper in controlled amounts. Copper can stabilize the austinite phase of the resultant alloy. The amount of copper is limited so that notch toughness, ductility and corrosion resistance of the alloy are not unduly affected in an adverse manner. Preferably, the alloy contains no more than about 2% copper, and more preferably not more than about 1% copper.

The alloy may include aluminum in controlled amounts. Preferably the amount of aluminum in the alloy is no more than about 1% in an effort to enhance stress corrosion resistance.

The alloy may also contain manganese and silicon in small amounts as a residual from smelting, such as an amount that together totals less than about 1%. Manganese and silicon can act as scavengers for impurities from the steel production process. Examples of such impurities include sulfur, phosphorous, carbon and nitrogen. These impurities, if present in uncontrolled amounts, can adversely affect the properties of the alloy.

The alloy also optionally includes other elements in small amounts (for example, in amounts less than about 1%), including elements known in the art for improving characteristics of stainless steel alloys. Examples of such elements include but are not limited to cobalt, niobium, tantalum, tungsten and vanadium.

Preferred and more preferred compositional ranges of the iron based alloy used in the orthodontic appliances of the present invention are set out below (the balance being essentially iron):

| Element | Preferred % by Wt. | More Preferred % by Wt. |
| --- | --- | --- |
| Cr | 10–13 | 11–12 |
| Ni | 9–12 | 10.5–11.5 |
| Ti | 1–4 | 1–2 |
| Mo | 0.5–2 | 0.5–1.5 |
| B | <0.01 | 0.001–0.005 |
| Cu | <2 | <1 |
| Al | <1 | <0.5 |
| Mn | <1 | <0.5 |
| Si | <0.5 | <0.25 |
| C | <0.03 | <0.02 |
| N | <0.03 | <0.02 |
| P | <0.04 | <0.02 |
| S | <0.02 | <0.01 |
| Nb | <0.5 | <0.1 |

The alloy of the present invention may be processed for machining and strengthening in the same manner as other known stainless steels. These methods commonly include a solution treatment of the alloying elements at an elevated temperature (e.g., 1800° F. or 980° C.), followed by quenching to room temperature, and then aging at an intermediate temperature (e.g., 1000° F. or 540° C.) to promote the precipitation of strengtheners. Using these conditions in a nitrogen atmosphere will produce an aesthetic titanium nitride coating on the appliance that exhibits a light gold or straw color. This coating may also include titanium aluminum nitride.

Optionally, the alloy can be subjected to a deep chill treatment or cryocooling treatment after quenching to further enhance the strength of the resultant alloy. The chill treatment cools the alloy to a temperature sufficiently below the martensite finish temperature to facilitate completion of the martensite transformation. An example of a suitable chilling process is to subject the alloy to a temperature below about −100° F. (−73° C.) for about 1 hour. This treatment will typically enhance the tensile strength of the alloy by a value of about 20,000 psi (1400 kg/cm$^3$).

Examples of suitable alloys and related processing methods are described in U.S. Pat. No. 5,681,528 which is incorporated by reference herein. Examples of suitable commercially-available alloys include Custom 465 brand stainless alloy from Carpenter Technology Corporation.

Orthodontic appliances according to the invention exhibit improved resistance to stress corrosion cracking resistance in comparison to conventional orthodontic appliances. Saliva and other oral fluids contain chlorides and present alkaline conditions which can adversely affect the corrosion resistance and strength of alloys that depend upon copper and/or aluminum precipitates for strengthening, such as stainless steel alloys 17-4 PH and 17-7 PH. Since titanium is relatively inert and relatively unaffected by chlorides and alkaline environments, orthodontic appliances made according to the invention have a higher resistance to stress corrosion cracking than appliances made of 17-4 PH and 17-7 PH stainless steel alloys.

Examples of orthodontic appliances constructed in accordance with the present invention include brackets, buccal tubes, cleats, lingual tubes, buttons, bite openers, Class II correction devices (e.g., Herbst appliances), facebows and archwires. The appliances exhibit higher strength in comparison to similar conventional appliances. As a result, the appliances of the invention can be made smaller than the size of similar conventional appliances and yet function as intended for the duration of the treatment program.

Figure 1B:
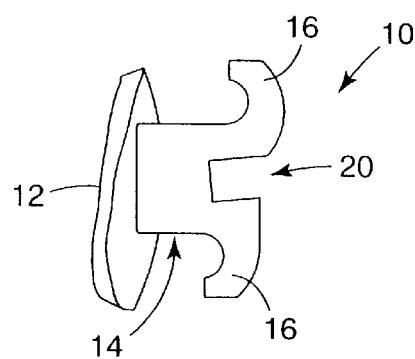
Figure 1C:
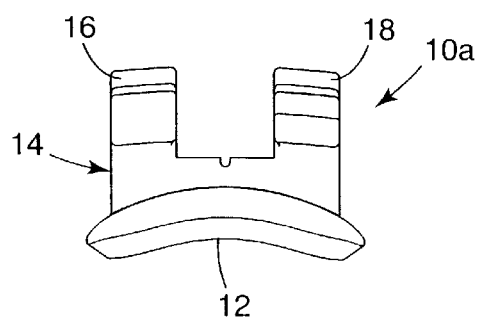

An example of a conventional prior art orthodontic appliance is illustrated in FIGS. 1A–1C and is designated by the numeral 10. The appliance 10 is known as an orthodontic bracket and has a base 12 for directly bonding the appliance 10 to a surface of a tooth. As is common with orthodontic brackets, the base 12 has a concave configuration adapted to match the convex external shape of the tooth surface upon which it is to be mounted.

The appliance 10 also includes a body 14 that extends outwardly from the base 12 in a buccolabial direction (i.e., in a direction extending toward the patient's cheeks or lips). The appliance 10 has a pair of mesial tiewings 16 that are located on a mesial side of the appliance 10 (i.e., on the side of the appliance 10 facing toward the middle of the patient's dental arch). The appliance 10 also includes a pair of distal tiewings 18 that are located on a distal side of the appliance 10 (i.e., on a side of the appliance 10 facing away from the middle of the patient's dental arch).

Each of the tiewings 16, 18 is connected to the body 14, and preferably is integrally connected to the body 14. Each of the tiewings 16, 18 presents an undercut area or notch for receiving a ligature (not shown). The ligature is utilized to retain an archwire into an archwire slot 20 of the appliance 10. The ligature can be in the form of an elastomeric O-ring or in the form of a wire tie. Typically, a wire tie is an initially straight section of fine metal wire that is subsequently twisted together at its ends.

The archwire slot 20 extends across the appliance 10 in a generally mesial-distal direction. The archwire slot 20 extends through the space between the pair of mesial tiewings 16 as well as through the space between the pair of distal tiewings 18. Optionally, but not necessarily, the bottom or lingual side (i.e., the side facing the patient's tongue) of the archwire slot 20 is inclined relative to the lingual side of the body 14, to facilitate torquing movements of the associated tooth. This angle of inclination is known as the "torque value" of the appliance 10. However, other constructions are also known, including constructions where the lingual side of the archwire slot 20 is parallel to the lingual side of the body 14 (in that instance, the torque value is zero).

Figure 2A:
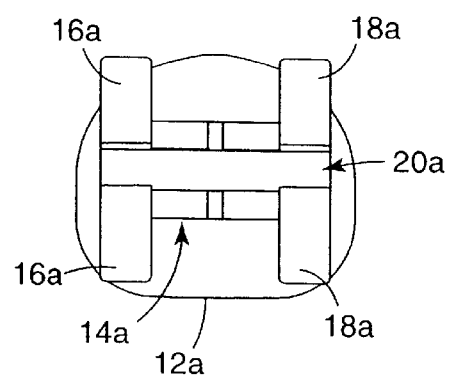
FIGS. 2A, 2B and 2C are front, end and side views respectively of an exemplary orthodontic appliances constructed in accordance with the present invention, and showing by comparison to FIGS. 1A–1C the relative size difference of various components of the appliance that are possible with the present invention.
Figure 2B:
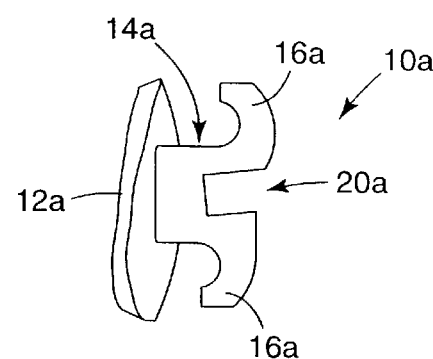
Figure 2C:
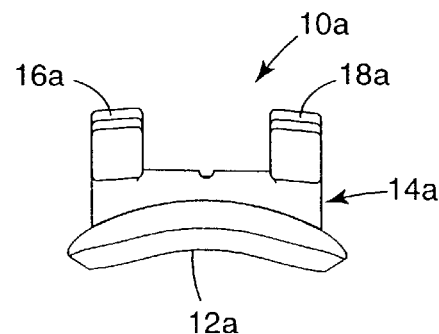

FIGS. 2A–2C are illustrations of an example of an orthodontic appliance 10*a* according to the present invention. The appliance 10*a* is made of a stainless steel alloy that includes precipitates of titanium, such as the alloys described above. A visual comparison of the appliance 10 shown in FIGS. 1A–1C to the appliance 10*a* shown in the corresponding FIGS. 2A–2C illustrates for exemplary purposes the reduction in size of various components of the appliance 10*a* that is possible in accordance with the principles of the present invention.

The appliance 10*a* includes a base 12*a* along with a body 14*a* that extends outwardly from the base 12*a* in a buccolabial direction. The appliance 10*a* also includes a pair of mesial tiewings 16*a* and a pair of distal tiewings 18*a*.

An archwire slot 20*a* extends across the body 14*a* in a generally mesial-distal direction. The archwire slot 20*a* extends through the space between the pair of mesial tiewings 16*a* and also through the space between the pair of distal tiewings 18a. In this example, the bottom or lingual side of the archwire slot 20a is inclined relative to a lingual side of the body 14a at an angle identical to the angle of inclination between the lingual side of the archwire slot 20 and the lingual side of the body 14. As a consequence, the appliance 10a a presents a torque value that is identical to the torque value of the appliance 10.

At least part of the appliance 10a is made of the high strength alloys mentioned above that include precipitates of titanium. In the embodiment illustrated, the body 14a is integrally connected to the tiewings 16a, 18a. The body 14a as well as the tiewings 16a, 18a are all made of the high strength alloy having the precipitates of titanium. However, other constructions are also possible, including brackets where only the body or only the tiewings are made of the high strength alloys mentioned above.

In the embodiment illustrated in FIGS. 2A–2C and like the appliance 10 described above, the base 12a is made as an option of a material different than the material of the body 14a and the tiewings 16a, 18a. For example, the base 12a could comprise a metal mesh-like structure that has small openings and resembles a fine wire screen. Optionally, the base 12a could include a foil backing layer between the mesh and the lingual side of the body 14a. As another option, the mesh could be chemically etched, provided with particles, sandblasted or otherwise treated to enhance the strength of the bond between the base 12a and the enamel layer of the patient's tooth.

To mount the appliance 10a on a tooth, a quantity of bonding adhesive is placed on the base 12a and the appliance 10a is then firmly pressed against the tooth enamel. During such bonding, a portion of the adhesive flows into the openings of the mesh. Once the adhesive has hardened, the mesh and the adhesive together establish a firm mechanical interlocking structure that helps retain the appliance 10a on the tooth.

The base 12a, when made of a mesh material described above, is fixedly secured to a lingual side of the body 14a, preferably by a brazing or welding process. However, other constructions are also possible. For example, the base 12a could be integrally connected to the body 14a and made of the same material as the material of the body 14a. In that instance, the base 12a is preferably provided with openings, protrusions, dovetail-shaped grooves, mushroom-shaped pegs or other recesses and/or overhanging structure in order to enhance the bond between the base 12a and the tooth enamel and provide a mechanical interlock once the adhesive has hardened.

The high-strength alloys as described above enable components of the appliance 10a to be reduced in size in comparison to corresponding components of the appliance 10. For example, the mesial-distal width of the tiewings 16a, 18a can be reduced by 30%, in comparison to the width of the tiewings 16, 18 when the latter are made of a 17-4 PH stainless steel. The relative difference in the width can be observed by comparing FIG. 2A with FIG. 1A, and by comparing FIG. 2C with FIG. 1C.

Additionally, the overall labial-lingual height of the appliance 10a (also known as the "in-out" dimension) is about 14% less than the corresponding dimension of the appliance 10. The difference in lingual-labial height can be observed by comparing FIG. 2B with FIG. 1B, and by comparing FIG. 2C with FIG. 1C. Again, the reduction in size is possible because of the higher yield strength of the stainless steel alloys with titanium precipitates, in comparison to the stainless steel alloys used in conventional orthodontic appliances such as the appliance 10.

Moreover, and as can be observed in FIG. 2A, the lingual side of the archwire slot 20a extends into the body 14a, including into middle areas of the body 14a located between the tiewings 16a, 18a. Such construction is possible in this example because the relatively high strength of the alloy helps to prevent collapse of the archwire slot 20a that might otherwise occur due to the forces present during orthodontic movement of the teeth.

By comparison, the archwire slot 20 of the appliance 10 is located a greater distance from the lingual side of the body 14 than the corresponding dimension of the appliance 10a to ensure that the archwire slot 20 does not normally collapse during treatment. As can be observed in FIG. 1A, the lingual side of the archwire slot 20 does not extend into the middle portion of the body 14 that is located between the tiewings 16, 18. Unfortunately, such increased lingual-labial orientation of the archwire slot 20 increases the likelihood that the appliance 10 will impinge against the patient's tissues or other oral structures during the course of treatment and cause the patient to experience discomfort.

Optionally, the appliance 10a has the same overall mesial-distal dimension as the appliance 10 as can be observed by comparing FIG. 2A with FIG. 1A, and by comparing FIG. 2C with FIG. 1C. Although a reduction in the mesial-distal overall width of the appliance 10a including the body 14a is possible, such construction is not presently preferred in general for twin brackets because the larger width provides greater control over rotational movements of the tooth about its long axis. However, the reduction in width of the individual tiewings 16a, 18a in a mesial-distal direction that is possible with the present invention is an advantage, in that greater space is presented between the tiewings 16a, 18a in a mesial-distal direction. Consequently, ligation of an archwire to the appliance 10a is facilitated in some instances.

As other options, the appliances 10a may be provided with hooks, removable pins or other structures as may be desired for connection to other orthodontic appliances in the oral cavity. Preferably, such hooks, pins and other structure are made of the same high-strength alloy having precipitates of titanium as mentioned above, and are preferably made of the same material as the material of the body 14a and the tiewings 16a, 18a. As such, those hooks, pins and other structure can be made somewhat smaller than would otherwise be possible, further reducing the likelihood that the patient will experience discomfort when used during the course of treatment.

Moreover, the reduced sections of the various components of the appliance 10a that is possible with the present invention enables in some instances the use of ligatures and auxiliaries having a somewhat larger cross-sectional area. For example, ligatures and force modules used in orthodontic treatment are often made of a resilient, elastomeric material that is stretched when installed to fit around tiewings, hooks or other structure of the appliance. Unfortunately, those elastomeric devices sometimes break, particularly when stretched during installation. By increasing the cross-sectional area of such elastomeric devices, the possibility of rupture is reduced. Accordingly, the smaller cross-sections of the various components of the appliance 10a is a distinct advantage, in that more space is available for receiving ligatures or other devices or components. As a result, those ligatures, devices or other components can have a larger cross-sectional area.

Figure 3:
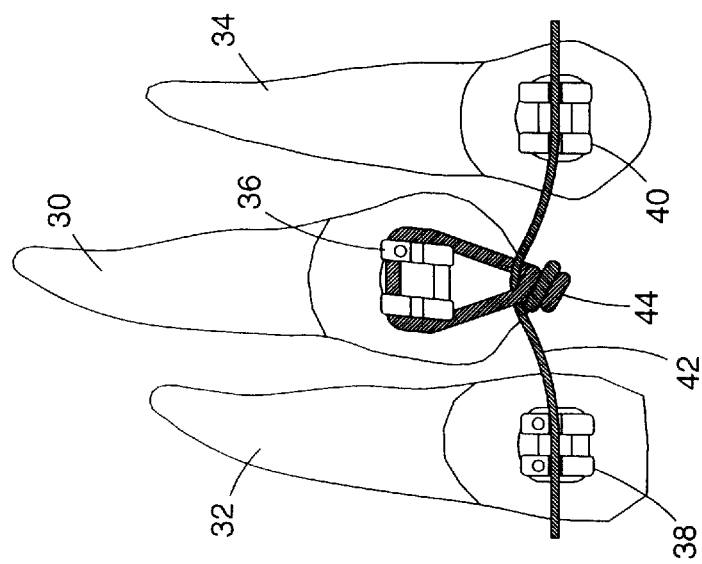
FIG. 3 is a reduced front elevational view showing three exemplary prior art orthodontic appliances mounted on three adjacent teeth, wherein an archwire has been inserted into slots of two of the appliances and a section of wire has been tied between the archwire and the appliance mounted on the malpositioned intermediate tooth in order to urge the intermediate tooth in an occlusal direction.

FIG. 3 illustrates an example of one type of orthodontic movement that is sometimes carried out during the course of treatment. In FIG. 3, an upper cuspid tooth 30 is malpositioned and located in a gingival direction (i.e., in a direction toward the patient's gums or gingiva) relative to an adjacent lateral tooth 32 and a first bicuspid tooth 34. In that instance, the practitioner may seek to extrude (i.e., move outwardly in an occlusal direction) the cuspid tooth 30 so that the cuspid tooth 30 is in alignment with the teeth 32, 34 and in a better position to occlude with an opposing tooth of the lower jaw.

In FIG. 3, cuspid bracket 36 is bonded to the cuspid tooth 30, a lateral bracket 38 is bonded to the lateral tooth 32 and a bicuspid bracket 40 is bonded to the bicuspid tooth 34. The brackets 36, 38, 40 are conventional brackets, such as brackets similar to the appliance 10 described above. In addition, an archwire 42 has been placed in the archwire slot of the brackets 38, 40.

Since the archwire slot of the bracket 36 is located a significant distance away from the archwire slot of the adjacent brackets 38, 40, a section of metal wire 44 is looped around the tiewings of the bracket 36 and the archwire 42 and tightened by twisting its ends together. When the wire section 44 is tightened in this manner, the archwire 42 bends as shown in FIG. 3. However, the inherent resiliency of the archwire 42 tends to restore the archwire 42 to a straight configuration. As the archwire 42 straightens, the archwire 42 urges the bracket 36 along with the cuspid tooth 30 in an occlusal direction.

Figure 4:
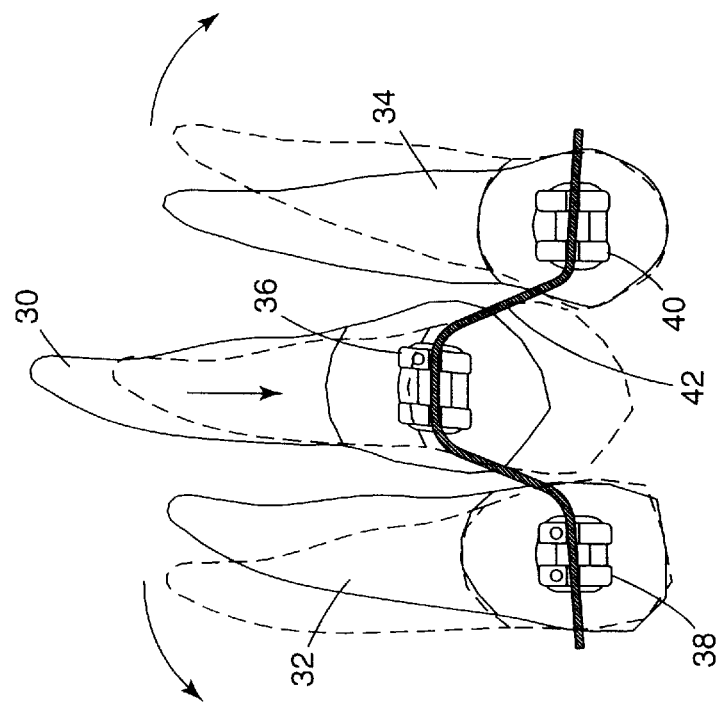
FIG. 4 is a view somewhat similar to FIG. 3 except that the archwire has been placed into the slot of the appliance mounted on the intermediate tooth, wherein arrows adjacent the remaining teeth illustrate the tipping movement of such teeth that is likely to occur in that instance.

In FIG. 4, brackets 36, 38, 40 are mounted on teeth 30, 32, 34 respectively and are identical to that shown in FIG. 3. However, in this instance, the archwire 42 has been inserted into the archwire slot of the cuspid bracket 36 as well as into the archwire slot of the brackets 38, 40. Unfortunately, by bending the archwire 42 to such a significant extent, the archwire 42 exerts a substantial tipping force on the brackets 38, 40 which, in turn, causes the teeth 32, 34 to pivot in the direction indicated by the curved arrows in FIG. 4. This pivoting movement shifts the teeth 32, 34 from their orientation as shown in full lines in FIG. 4 toward the orientation shown in dashed lines in FIG. 4. Although the cuspid tooth 30 will tend to extrude in this circumstance, the resulting positions of the lateral tooth 32 and the first bicuspid tooth 34 are generally deemed unsatisfactory.

Figure 5:
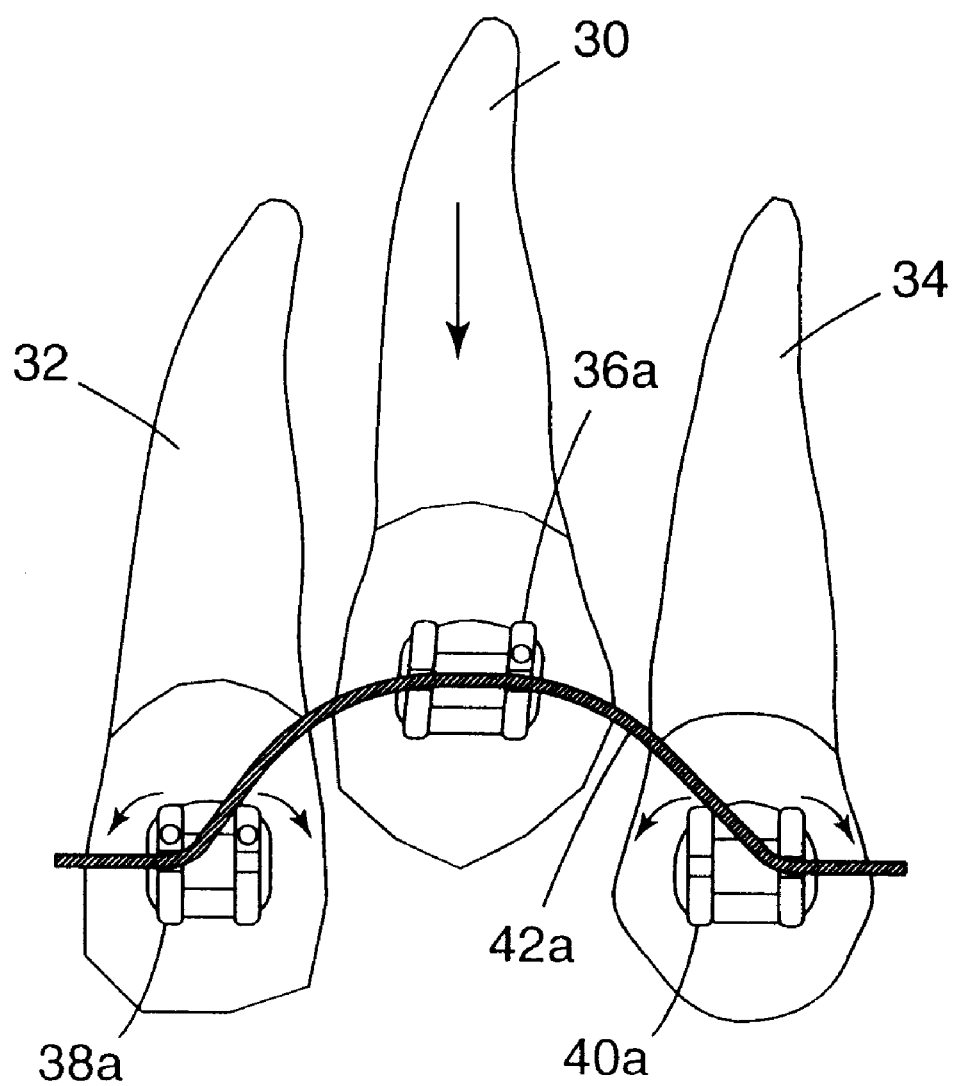
FIG. 5 is a view somewhat similar to FIG. 4 except that the three orthodontic appliances shown in FIG. 4 have been replaced with orthodontic appliances constructed according to the present invention, and depicting the archwire connected to the appliances on the two outer teeth in a somewhat different manner than that shown in FIGS. 3 and 4 so that the intermediate tooth can be moved in an occlusal direction without exerting undue tipping forces on the remaining two teeth.

FIG. 5 is an illustration somewhat similar to FIGS. 3 and 4, except showing appliances according to the present invention. In particular, a cuspid bracket 36a is mounted on cuspid tooth 30, a lateral bracket 38a is mounted on lateral tooth 32, and a bicuspid bracket 40a is mounted on first bicuspid tooth 34. The brackets 36a, 38a, 40a are mounted on the corresponding teeth in locations identical to the locations of the brackets 36, 38, 40 on the teeth shown in FIGS. 5 and 6.

However, the brackets 36a, 38a, 40a are constructed using the high-strength stainless steel alloy having precipitates of titanium as described above. As such, a larger space is provided between mesial and distal tiewings of the brackets 36a, 38a, 40a. An archwire 42a is identical to the archwire 42, but in this instance is placed in the archwire slots of the brackets 36a, 38a, 40a in a somewhat different manner.

In particular, and as depicted in FIG. 5, the archwire 42a is inserted into the portion of the archwire slot of the lateral bracket 38a that is located between the pair of mesial tiewings, but is not placed in the portion of the archwire slot that is located between the pair of distal tiewings of the bracket 38a. Instead, the archwire 42a extends upwardly and in a gingival direction in the space located in the middle of the bracket 38a between the mesial and distal tiewings.

Similarly, the archwire 42a is placed in a portion of the archwire slot of the first bicuspid bracket 40a that is located between the pair of distal tiewings, but not in that portion of the archwire slot that is located in the space between the mesial tiewings of that bracket. Instead, the archwire 42a extends upwardly and in a gingival direction in the central portion of the bracket 40a that is located between the mesial and distal tiewings. The archwire 42a is also placed in the archwire slot of the cuspid bracket 36a along its entire mesial-distal length.

As shown by the arrows adjacent the brackets 38a, 40a in FIG. 5, the forces exerted by the archwire 42a in that orientation on the brackets 38a, 40a are generally balanced in such a manner that the associated teeth 32, 34 do not tend to pivot. For example, the force exerted by the archwire 42a on the mesial tiewings of the lateral bracket 38a is opposed by the force of the archwire 42a bearing against the inner gingival corner of the distal tiewing located on the gingival side of the bracket 38a. A similar but mirror-image effect is also noted in connection with the first bicuspid bracket 40a.

An orthodontic appliance 10b according to another embodiment of the invention is illustrated in FIGS. 6A, 6B and 6C. The appliance 10b includes a base 12b that is preferably identical or similar to the base 12a described above. The appliance 10b also includes a body 14b that is connected to the base 12b. The appliance 10b also has an archwire slot 20b.

The appliance 10b has a pair of gingival tiewings 15b, one of which is adjacent a mesial end of the body 14b and the other of which is adjacent a distal end of the body 14b. The tiewings 15b are integrally connected to the body 14b. However, the appliance 10b lacks conventional tiewings extending from the body 14b in an occlusal direction. Instead, the body 14b has a pair of occlusal tiewings 46b that are turned outward. Beneath each tiewing 46b is a notch 17b that is located adjacent the base 12b.

The notches 17b have dimensions adapted to receive a ligature, such as an elastomeric ligature that is also extended around the gingival tiewings 15b. The notches 17b are located in a lingual direction relative to the lingual side of an archwire slot 20b, although other constructions are also possible. Optionally, and as shown in FIGS. 6B and 6C, an outer portion of the notches 17b extends beneath the archwire slot 20b.

The appliance 10b is a significant advantage in instances where it is desired to limit extension of the appliance in an occlusal direction. For example, in instances where the teeth overlap and the appliance 10b is mounted on one of the patient's lower teeth, the lack of occlusal tiewings helps prevent contact of the appliance 10b with the opposing tooth when the patient's jaws are closed. The relatively high strength of the alloy of the appliance 10b allows provision of the notch 17b while preventing collapse of the archwire slot 20b during the course of treatment.

The appliance 10b as illustrated in FIGS. 6A–6C is an example of a construction not feasible in the past when manufactured to relatively small overall dimensions. For example, if an appliance similar in configuration to the appliance 10b were made of a 17–4 PH stainless steel alloy, such an appliance may fracture in an area beneath the notches 17b and the archwire slot 20b when subjected to the forces encountered during orthodontic treatment. However, since the preferred alloys as described above provide greater strength, construction of the appliance 10b according to the invention yields a structure that can withstand the forces encountered during orthodontic treatment, even when having only relatively small overall dimensions.

As can be appreciated, the various cross sectional areas of the components of the orthodontic appliances of the invention can be smaller than corresponding cross-sectional areas of components of similar appliances, because of the increased yield strength of the stainless steel alloy having precipitates of titanium. Accordingly, the present invention allows construction of appliances and various components of appliances in a manner heretofore unknown in the art. Similar advantages are used when the appliance is an orthodontic buccal tube, button, cleat, pin or other device.

Moreover, the relatively small size of appliances constructed in accordance with the present invention is an advantage in that the appliances are more difficult to see when in place during treatment. Such reduced size decreases the likelihood that a casual observer will notice the appliances in use. In the past, many patient's have complained about a "metal mouth" appearance provided by conventional appliances, and the present invention overcomes that objection at least in part.

Other advantages are also realized by use of the present invention. For example, appliances having a reduced overall size are more hygienic, since less area is available for plaque to form.

A number of variations and modifications of the invention are possible. For example, the alloy as described above can be used with other orthodontic devices such as archwires and facebows as well. For that reason, the invention should not be deemed limited to the specific embodiments that are described above in detail, but instead only by a fair scope of the claims that follow along with their equivalents.

What is claimed is:

1. An orthodontic appliance selected from the group consisting essentially of brackets, buccal tubes, cleats, lingual tubes, buttons, bite openers, Class II correction devices, facebows and archwires, wherein the appliance is made of an iron-based alloy that includes precipitates of titanium in an amount effective to strengthen the alloy.

2. An orthodontic appliance according to claim 1 wherein the appliance is an orthodontic bracket.

3. An orthodontic appliance according to claim 1 wherein the appliance is a buccal tube.

4. An orthodontic appliance according to claim 1 wherein the appliance is an archwire.

5. An orthodontic appliance according to claim 1 wherein the appliance is a facebow.

6. An orthodontic bracket comprising:
   a base;
   a body extending from the base; and
   an archwire slot extending across the body, wherein the body is made of an iron-based alloy that includes precipitates of titanium in an amount effective to strengthen the alloy.

7. An orthodontic bracket according to claim 6 wherein the bracket includes at least one tiewing that extends outwardly from the body and is integrally connected to the body.

8. An orthodontic appliance selected from the group consisting essentially of brackets, buccal tubes, cleats, lingual tubes, buttons, bite openers, Class II correction devices, facebows and archwires, wherein the appliance includes a body consisting essentially of, in weight percent, about

| | |
|---|---|
| Cr | 10–13 |
| Ni | 9–12 |
| Ti | 1–4 |
| Mo | 0.5–2 |
| B | <0.01 |
| Mn | <1 |
| Si | <0.5 |
| C | <0.03 |
| N | <0.03 |
| P | <0.04 |
| S | <0.02 |
| Nb | <0.5 | the balance being iron.

9. An orthodontic appliance selected from the group consisting essentially of brackets, buccal tubes, cleats, lingual tubes, buttons bite openers, Class II correction devices, facebows and archwires, wherein the appliance includes a body consisting essentially of, in weight percent, about

| | |
|---|---|
| Cr | 11–12 |
| Ni | 10.5–11.5 |
| Ti | 1–2 |
| Mo | 0.5–1.5 |
| B | 0.001–0.005 |
| Cu | <1 |
| Al | <0.5 |
| Mn | <0.5 |
| Si | <0.25 |
| C | <0.02 |
| N | <0.02 |
| P | <0.02 |
| S | <0.01 |
| Nb | <0.1 | the balance being iron.

* * * * *